United States Patent
Starck et al.

(10) Patent No.: US 8,293,775 B2
(45) Date of Patent: Oct. 23, 2012

(54) BENZOXAZOLONE DERIVATIVES, PROCESSES FOR PREPARING THEM AND THEIR USES

(75) Inventors: Jean-Philippe Starck, Gougenheim (FR); Benoît Kenda, Emines (BE)

(73) Assignee: UCB Pharma, S.A., Brussels (BE)

( * ) Notice: Subject to any disclaimer, the term of this patent is extended or adjusted under 35 U.S.C. 154(b) by 1424 days.

(21) Appl. No.: 11/569,605

(22) PCT Filed: May 24, 2005

(86) PCT No.: PCT/EP2005/005596
§ 371 (c)(1), (2), (4) Date: Aug. 28, 2007

(87) PCT Pub. No.: WO2005/118561
PCT Pub. Date: Dec. 15, 2005

(65) Prior Publication Data
US 2007/0299118 A1 Dec. 27, 2007

(30) Foreign Application Priority Data
May 27, 2004 (EP) ...................................... 04012573

(51) Int. Cl.
*C07D 263/58* (2006.01)
*A61K 31/423* (2006.01)
(52) U.S. Cl. ....................................... 514/375; 548/221
(58) Field of Classification Search .................. 514/375, 514/376; 548/221
See application file for complete search history.

(56) References Cited

U.S. PATENT DOCUMENTS

| 7,632,856 B2 | 12/2009 | Kenda et al. |
| 2005/0250794 A1 * | 11/2005 | Napper et al. ............. 514/260.1 |

FOREIGN PATENT DOCUMENTS

| EP | 0 673 933 A | 9/1995 |
| EP | 1719761 A1 | 11/2006 |
| WO | 94/29272 A | 12/1994 |
| WO | 00/29397 A | 5/2000 |
| WO | 03/076420 A | 9/2003 |

OTHER PUBLICATIONS

Kalcehva et al. Chem. Heterocycl. Compd., 1985, 21, 985-987.*
Steinberger et al. Neurology, 2000, 55, 1735-1737.*
Stern, Parkinsonism and Related Disoders, 2001, 7, 27-33.*
*Daiichi Sankyo Company, LTD.* v. *Matrix Laboratories, LTD.*, U.S. Court of Appeals for the Federal Circuit (decided Sep. 9, 2010).*
Kalcheva et al., "Synthesis of N-Substituted 2-Benzoxalones", Chem. Heterocycl. Compd., 1985, 985-987, 21(9).

* cited by examiner

*Primary Examiner* — Joseph Kosack
*Assistant Examiner* — Matthew P Coughlin
(74) *Attorney, Agent, or Firm* — McDonnell Boehnen Hulbert & Berghoff LLP

(57) ABSTRACT

The present invention relates to benzoxazolone derivatives, processes for preparing them, pharmaceutical compositions containing them and their use as pharmaceuticals, in the treatment of movement disorders, in particular in Parkinson's disease.

5 Claims, No Drawings

BENZOXAZOLONE DERIVATIVES, PROCESSES FOR PREPARING THEM AND THEIR USES

The present invention concerns benzoxazolone derivatives, processes for preparing them, pharmaceutical compositions containing them and their use as pharmaceuticals.

Movement and other disorders due to dysfunction of the basal ganglia and related brain structures are of major socio-economic importance. Such disorders can occur as a consequence of inherited or acquired disease, idiopathic neurodegeneration or they may be iatrogenic. The spectrum of disorders is very diverse, ranging from those associated with poverty of movement (akinesia, hypokinesia, bradykinesia, e.g. in parkinsonian symptomatology), hypertonia (e.g. Parkinson's disease, spasticity) to the involuntary movement disorders (hyperkinesias or dyskinesia, e.g. Huntington's disease, dyskinesia induced by L-3,4-dihydroxyphenylalanine (L-DOPA or levodopa), tardive dyskinesia, progressive supernuclear palsy, multiple system atrophy, corticobasal degeneration, Wilson's disease, progressive pallidal atrophy, the dystonias, metabolic neurotransmitter diseases, tics, tremor, Tourette's syndrome, Sydenham's chorea, restless legs syndrome (RLS), chorea and choreathetosis, paroxysmal dyskinesias, myoclonic disorders, Rett syndrome).

Parkinson's disease and related conditions are amongst of the most prevalent diseases associated with poverty of movement. Parkinsonian symptoms are characterized by slowness of movement (bradykinesia), rigidity and/or tremor. Parkinsonian symptoms are seen in a variety of conditions, most commonly in idiopathic parkinsonism (i.e. Parkinson's Disease) but also following treatment of schizophrenia (i.e. neuroleptic-induced parkinsonism), exposure to toxins/drugs and head injury.

It is widely appreciated that the primary pathology underlying Parkinson's disease is degeneration, in the brain, of the dopaminergic projections from the substantia nigra to the striatum. This has led to the widespread use of dopamine-replacing agents (e.g. L-3,4-dihydroxyphenylalanine (L-DOPA) and dopamine agonists) as symptomatic treatments for Parkinson's disease.

L-DOPA therapy currently offers the best symptomatic treatment of Parkinson's disease and a variety of other movement disorders and most patients will require it during the course of their disease. However, patients will develop L-DOPA-associated motor complications. Problems can include motor fluctuations (e.g. delayed "on" response and dose failure, end-of-dose wearing-off, unpredictable "on-off" response, freezing episodes) and the appearance of a range of side-effects which manifest as abnormal involuntary movements, such as dyskinesia (e.g. peak-dose dyskinesia, "off" dystonia, diphasic dyskinesia). Dyskinesias are usually dystonic or choreiform in nature.

The phenomenon of "end-of-dose wearing-off" generally occurs early in the course of the disease. This is the most common and usually the first type of motor fluctuation that develops. As the name implies, the patient develops a loss of response to a dose of medication before taking the next dose. This occurs more often with levodopa than with the dopamine agonists because the agonists have a significantly longer half-life. Over time, fluctuation from mobility to immobility occurs more frequently, becoming more abrupt and disabling. The response to treatment can become unpredictable, many doses of levodopa having a delayed effect or even no effect at all.

Although many attempts have been made to develop agents that will prevent the development an/or the expression of dyskinesias, just a few were made to find a therapeutic tool able to manage motor fluctuations. Until now, only two classes of drug compounds, the catechol-O-methyltransferase (COMT) and monoamine oxydase type B ($MAO_B$) inhibitors, were developed to lengthen the beneficial therapeutic effect of L-DOPA but some of these compounds show adverse effects.

There is therefore, a need for new add-on therapies to L-DOPA which can enhance its efficacy and/or reduce its adverse effects.

Acta Poloniae Pharm. 1989, 46(2), 114-118, discloses 2-oxo-1,3-benzoxazol-3(2H)-yl)acetamide, 5-chloro-2-oxo-3(2H)-benzoxazoleacetamide and 6-chloro-2-oxo-1,3-benzoxazol-3(2H)-yl)acetamide as synthesis intermediates in the synthesis of N-carbamoylmethyl derivatives.

J. Prakt. Chem. 1966, 33(3-4), 130-138, discloses 2-oxo-1,3-benzoxazol-3(2H)-yl)acetamide as a synthesis intermediate in the synthesis of (benzoxazolon-3-yl)-carboxylic acids.

Godishnik na Sofiiskiya Universitet Sv. Kliment Okhridski, Khimicheski Fakultet (1979), Volume Date 1975-1976, 70, Pt. 2, 35-9, discloses N-methyl-2-oxo-3(2H)-benzoxazoleacetamide.

Khimiya Geterostsiklicheskikh Soedinenii (1985), (9), 1185-8, discloses: 6-bromo-5-chloro-N-methyl-2-oxo-3(2H)-benzoxazoleacetamide; 6-bromo-N-methyl-2-oxo-3(2H)-benzoxazoleacetamide; 6-chloro-N-methyl-2-oxo-3(2H)-benzoxazoleacetamide; 5-chloro-N-methyl-2-oxo-3(2H)-benzoxazoleacetamide and N-methyl-2-oxo-3(2H)-benzoxazoleacetamide.

Uzbekskii Khimicheskii Zhumal (1988), (1), 70 discloses: N-methyl-2-oxo-3(2H)-benzoxazoleacetamide and N-(1,1-dimethylethyl)-2-oxo-3(2H)-benzoxazoleacetamide.

Zhurnal Vsesoyuznogo Khimicheskogo Obshchestva im. D. I. Mendeleeva (1987), 32(3), 342-4, discloses: 6-bromo-N,N-diethyl-2-oxo-3(2H)-benzoxazoleacetamide; 6-chloro-N,N-diethyl-2-oxo-3(2H)-benzoxazoleacetamide; N,N-diethyl-2-oxo-3(2H)-benzoxazoleacetamide; 6-bromo-N,N-dibutyl-2-oxo-3(2H)-benzoxazoleacetamide; N,N-dibutyl-6-chloro-2-oxo-3(2H)-benzoxazoleacetamide and N,N-dibutyl-2-oxo-3(2H)-benzoxazoleacetamide.

Database Crossfire Beilstein Institute for Organic Chemistry, XP002300055 (BRN: 4485565) describes 6-bromo-5-chloro-3-(methylcarbamoylmethyl)-2-benzoxazolone.

The following compounds are disclosed in chemical libraries: 5-bromo-2-oxo-3(2H)-benzoxazoleacetamide; 6-bromo-2-oxo-3(2H)-benzoxazoleacetamide; 2-oxo-N-propyl-3(2H)-benzoxazoleacetamide; N,N-bis(2-methylpropyl)-6-chloro-2-oxo-3(2H)-benzoxazoleacetamide; 6-chloro-2-oxo-N-propyl-3(2H)-benzoxazoleacetamide; N-(1-methylethyl)-2-oxo-3(2H)-benzoxazoleacetamide; 6-chloro-N-(1-methylethyl)-2-oxo-3(2H)-benzoxazoleacetamide; 6-chloro-N-(1,1-dimethylethyl)-2-oxo-3(2H)-benzoxazoleacetamide; 5-chloro-2-oxo-1,3-benzoxazol-3(2H)-yl-N-(1,1-dimethylethyl)acetamide; 2-oxo-1,3-benzoxazol-3(2H)-yl-N-(1-methylpropyl)acetamide; 6-chloro-N,N-dimethyl-2-oxo-3(2H)-benzoxazoleacetamide and N,N-dimethyl-2-oxo-3(2H)-benzoxazoleacetamide.

It is known from the international patent application WO 00/29397 that piperazine and piperidine derivatives have anti-anxiety and anti-depression activities.

It is known from the international patent application WO 94/29272 that 1-substituted isatin and oxindole derivatives are of value in the treatment of the cognitive dysfunctions.

It is known from the international patent application WO 03/076420 that cyclic amide derivatives are of value in the treatment of neurodegenerative diseases.

It is known from the European patent application EP 0 673 933 that aminoalkyl benzoxazolinone and benzothiazolinone derivatives have anti-anxiety activity and psychotropic activity.

It has now surprisingly been found that certain benzoxazolone derivatives demonstrate therapeutic properties which render them useful in a variety of pharmaceutical indications, and particularly for the symptomatic and/or prophylactic treatment of movement disorders and/or motor fluctuations, in particular in Parkinson's disease.

In one aspect the invention therefore provides a compound having formula I or a pharmaceutically acceptable salt thereof,

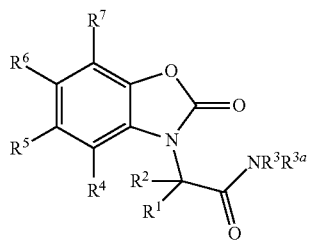

wherein
$R^1$ is hydrogen or $C_{1-4}$-alkyl unsubstituted or substituted by hydroxy;
$R^2$ is hydrogen or $C_{1-4}$-alkyl unsubstituted or substituted by hydroxy;
$R^3$ is hydrogen or unsubstituted $C_{1-4}$-alkyl;
$R^{3a}$ is hydrogen or unsubstituted $C_{1-4}$-allyl;
$R^4$ is hydrogen, halogen, or $C_{1-4}$-alkoxy unsubstituted or substituted by a phenyl group;
$R^5$ is hydrogen, halogen, or $C_{1-4}$-alkoxy unsubstituted or substituted by a phenyl group;
$R^6$ is hydrogen, halogen, or $C_{1-4}$-alkoxy unsubstituted or substituted by a phenyl group;
$R^7$ is hydrogen, halogen, or $C_{1-4}$-alkoxy unsubstituted or substituted by a phenyl group;
with the proviso that if $R^1$, $R^2$, $R^4$, $R^5$ and $R^7$ are hydrogen, then $R^6$ is not hydrogen, bromo or chloro; and if $R^1$, $R^2$, $R^4$, $R^6$ and $R^7$ are hydrogen, then $R^5$ is not bromo or chloro; and if $R^1$, $R^2$, $R^3$, $R^4$ and $R^7$ are hydrogen, $R^6$ is bromo, and $R^5$ is chloro, then $R^{3a}$ is not methyl.

In another aspect the invention provides 2-(6-bromo-2-oxo-1,3-benzoxazol-3(2H)-yl)-N,N-dimethylacetamide.

The term "halogen", as used herein, includes chloro, bromo, fluoro, iodo. Preferred halogens are chloro, bromo, and fluoro.

The term "hydroxy", as used herein, represents a group of formula —OH.

The term "$C_{1-4}$-alkoxy", as used herein, represents a group of formula —$OR^a$ wherein $R^a$ is a $C_{1-4}$-alkyl group, optionally substituted by 1 to 3 substituents selected from halogen or a phenyl group. The preferred $C_{1-4}$-alkoxy group is methoxy.

The term "$C_{1-4}$-alkyl", as used herein, is defined as including saturated, monovalent hydrocarbon radicals having straight or branched moieties and containing 1-4 carbon atoms. Any alkyl moiety may optionally be substituted by 1 to 5 substituents selected independently from hydroxy, halogen or a phenyl group. The preferred alkyl group is methyl.

The term "phenyl group", as used herein, represents an organic radical derived from an aromatic hydrocarbon consisting of a ring and containing 6 carbon atoms by removal of one hydrogen, and optionally substituted by 1 to 3 substituents selected from halogen, $C_{1-4}$-alkyl, $C_{1-4}$-alkoxy or cyano.

The term "cyano" as used herein, represents a group of the formula —CN.

Generally, $R^1$ is hydrogen or $C_{1-4}$-alkyl unsubstituted or substituted by hydroxy. Preferred $R^1$ is hydrogen.

Generally, $R^2$ is hydrogen or $C_{1-4}$-alkyl unsubstituted or substituted by hydroxy. Preferred $R^2$ is hydrogen.

Generally, $R^3$ is hydrogen or unsubstituted $C_{1-4}$-alkyl. Preferred $R^3$ is hydrogen or methyl. More preferred $R^3$ is hydrogen.

Generally, $R^{3a}$ is hydrogen or unsubstituted $C_{1-4}$-alkyl. Preferred $R^{3a}$ is hydrogen or methyl. More preferred $R^{3a}$ is hydrogen.

Generally, $R^4$ is hydrogen, halogen, or $C_{1-4}$-alkoxy unsubstituted or substituted by a phenyl group. Usually, $R^4$ is hydrogen and halogen. Preferred $R^4$ is hydrogen and chloro. More preferred $R^4$ is hydrogen.

Generally, $R^5$ is hydrogen, halogen, or $C_{1-4}$-alkoxy unsubstituted or substituted by a phenyl group. Usually, $R^5$ is hydrogen and halogen. Preferred $R^5$ is hydrogen and fluoro. More preferred $R^5$ is hydrogen.

Generally, $R^6$ is hydrogen, halogen, or $C_{1-4}$-alkoxy unsubstituted or substituted by a phenyl group. Usually, $R^6$ is hydrogen, halogen or unsubstituted $C_{1-4}$-alkoxy. Preferred is hydrogen, fluoro, bromo, chloro and methoxy. More preferred $R^6$ is hydrogen, fluoro, chloro and methoxy.

Generally, $R^7$ is hydrogen, halogen, or $C_{1-4}$-alkoxy unsubstituted or substituted by a phenyl group. Usually, $R^7$ is hydrogen, halogen or unsubstituted $C_{1-4}$-alkoxy. Preferred $R^7$ is hydrogen, fluoro, bromo, chloro and methoxy. More preferred $R^7$ is hydrogen, fluoro, bromo and chloro.

Combinations of one or more of these preferred compound groups are especially preferred.

In another aspect the invention therefore provides a compound having formula I or a pharmaceutically acceptable salt thereof, with the proviso that if $R^1$, $R^2$, $R^4$, $R^5$ and $R^7$ are hydrogen, then $R^6$ is not hydrogen, bromo or chloro; and if $R^1$, $R^2$, $R^4$, $R^6$ and $R^7$ are hydrogen, then $R^5$ is not bromo or chloro; and if $R^1$, $R^2$, $R^4$ and $R^7$ are hydrogen, and $R^6$ is bromo, then $R^5$ is not chloro.

In another aspect the invention therefore provides a compound having formula I or a pharmaceutically acceptable salt thereof, with the proviso that if $R^1$, $R^2$, $R^4$ and $R^7$ are hydrogen, then $R^5$ and/or $R^6$ are not hydrogen, bromo or chloro.

In one embodiment of the invention, the compounds of formula I, or pharmaceutically acceptable salts thereof, are those wherein
$R^1$ is hydrogen;
$R^2$ is hydrogen;
$R^3$ is selected from hydrogen or unsubstituted $C_{1-4}$-alkyl;
$R^{3a}$ is selected from hydrogen or unsubstituted $C_{1-4}$-alkyl;
$R^4$ is selected from hydrogen or halogen;
$R^5$ is selected from hydrogen or halogen;
$R^6$ is selected from hydrogen, halogen or unsubstituted $C_{1-4}$-alkoxy;
$R^7$ is selected from hydrogen, halogen or unsubstituted $C_{1-4}$-alkoxy;
with the proviso that if $R^4$, $R^5$ and $R^7$ are hydrogen, then $R^6$ is not hydrogen, bromo or chloro; and if $R^4$, $R^6$ and $R^7$ are hydrogen, then $R^5$ is not bromo or chloro; and if $R^3$, $R^4$ and $R^7$ are hydrogen, $R^6$ is bromo, and $R^5$ is chloro, then $R^{3a}$ is not methyl.

In a preferred embodiment of the invention, the compounds of formula I, or pharmaceutically acceptable salts thereof, are those wherein
$R^1$ is hydrogen;
$R^2$ is hydrogen;

$R^3$ is selected from hydrogen or methyl;
$R^{3a}$ is selected from hydrogen or methyl;
$R^4$ is hydrogen or chloro;
$R^5$ is hydrogen or fluoro;
$R^6$ is selected from hydrogen, fluoro, chloro, bromo or methoxy;
$R^7$ is selected from hydrogen, fluoro, chloro, bromo or methoxy;
with the proviso that if $R^4$, $R^5$ and $R^7$ are hydrogen, then $R^6$ is not hydrogen, bromo or chloro; and if $R^4$, $R^6$ and $R^7$ are hydrogen, then $R^5$ is not bromo or chloro; and if $R^3$, $R^4$ and $R^7$ are hydrogen, $R^6$ is bromo, and $R^5$ is chloro, then $R^{3a}$ is not methyl.

In a more preferred embodiment of the invention, the compounds of formula I, or pharmaceutically acceptable salts thereof, are those wherein
$R^1$ is hydrogen;
$R^2$ is hydrogen;
$R^3$ is selected from hydrogen or methyl;
$R^{3a}$ is selected from hydrogen or methyl;
$R^4$ is hydrogen;
$R^5$ is hydrogen;
$R^6$ is selected from hydrogen, fluoro, chloro, or methoxy;
$R^7$ is selected from hydrogen, fluoro, chloro, or bromo;
with the proviso that if $R^7$ is hydrogen, then $R^6$ is not hydrogen or chloro.

Preferred individual compounds of the invention are:
2-(6-methoxy-2-oxo-1,3-benzoxazol-3(2H)-yl)acetamide;
2-(6-fluoro-2-oxo-1,3-benzoxazol-3(2H)-yl)acetamide;
2-(7-fluoro-2-oxo-1,3-benzoxazol-3(2H)-yl)acetamide;
2-(5,6-difluoro-2-oxo-1,3-benzoxazol-3(2H)-yl)acetamide;
2-(6-bromo-7-fluoro-2-oxo-1,3-benzoxazol-3(2H)-yl)acetamide;
2-(7-chloro-2-oxo-1,3-benzoxazol-3(2H)-yl)acetamide;
2-(6-bromo-7-chloro-2-oxo-1,3-benzoxazol-3(2H)-yl)acetamide;
2-(6,7-dichloro-2-oxo-1,3-benzoxazol-3(2H)-yl)acetamide;
2-(6,7-difluoro-2-oxo-1,3-benzoxazol-3(2H)-yl)acetamide;
2-(6-chloro-7-fluoro-2-oxo-1,3-benzoxazol-3(2H)-yl)acetamide;
2-(7-bromo-2-oxo-1,3-benzoxazol-3(2H)-yl)acetamide;
2-(6,7-dibromo-2-oxo-1,3-benzoxazol-3(2H)-yl)acetamide;
2-(7-bromo-6-chloro-2-oxo-1,3-benzoxazol-3(2H)-yl)acetamide;
2-(7-methoxy-2-oxo-1,3-benzoxazol-3(2H)-yl)acetamide;
2-(4-chloro-6,7-difluoro-2-oxo-1,3-benzoxazol-3(2H)-yl)acetamide;
2-(6-bromo-2-oxo-1,3-benzoxazol-3(2H)-yl)-N,N-dimethylacetamide.

More preferred compounds of the invention:
2-(6-methoxy-2-oxo-1,3-benzoxazol-3(2H)-yl)acetamide;
2-(6-fluoro-2-oxo-1,3-benzoxazol-3(2H)-yl)acetamide;
2-(7-fluoro-2-oxo-1,3-benzoxazol-3(2H)-yl)acetamide;
2-(7-chloro-2-oxo-1,3-benzoxazol-3(2H)-yl)acetamide;
2-(7-bromo-2-oxo-1,3-benzoxazol-3(2H)-yl)acetamide; and
2-(6,7-difluoro-2-oxo-1,3-benzoxazol-3(2H)-yl)acetamide.

Most preferred compounds of the invention:
2-(6-methoxy-2-oxo-1,3-benzoxazol-3(2H)-yl)acetamide;
2-(6-fluoro-2-oxo-1,3-benzoxazol-3(2H)-yl)acetamide;
2-(7-fluoro-2-oxo-1,3-benzoxazol-3(2H)-yl)acetamide;
2-(7-bromo-2-oxo-1,3-benzoxazol-3(2H)-yl)acetamide; and
2-(6,7-difluoro-2-oxo-1,3-benzoxazol-3(2H)-yl)acetamide.

The "pharmaceutically acceptable salts" according to the invention include therapeutically active, non-toxic base salt forms which the compounds of formula I are able to form.

For example the compounds of formula I containing acidic protons may be converted into their therapeutically active, non-toxic base addition salt forms, e.g. metal or amine salts, by treatment with appropriate organic and inorganic bases. Appropriate base salt forms include, for example but not limited to, ammonium salts, alkali and alkaline earth metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate acid.

Compounds of the formula I and their salts can be in the form of solvates, which are included within the scope of the present invention. Such solvates include for example hydrates, alcoholates and the like.

Some of the compounds of formula I and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula I or mixtures thereof (including all possible mixtures of stereoisomers).

Some of the compounds of formula I may also exist in tautomeric forms. Such forms although not explicity indicated in the above formula are intended to be included within the scope of the present invention.

With respect to the present invention reference to a compound or compounds is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of formula I according to the invention can be prepared analogously to conventional methods as understood by the person skilled in the art of synthetic organic chemistry.

According to one embodiment, some compounds having the general formula I may be prepared by alkylation of a compound of formula II with a compound of formula III according to the equation:

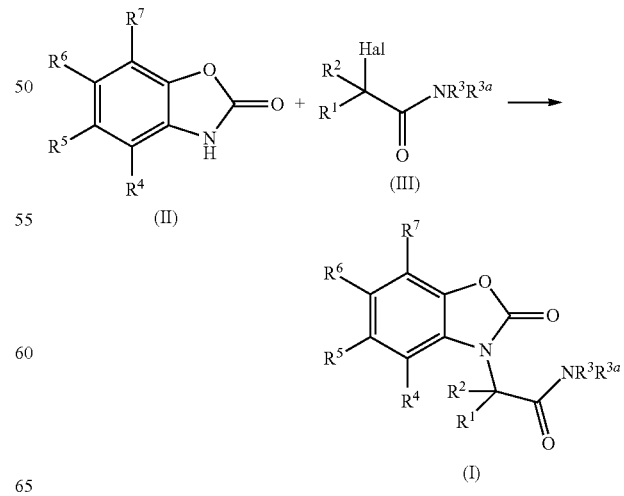

wherein Hal is an halogen atom, preferably bromo or chloro.

This reaction may be carried out in the presence of a strong base, preferably sodium hydride, at a temperature between 0 and 40° C., in an inert solvent, for example DMF, under an inert atmosphere, or as described in the British patent GB 1,309,692.

Compounds of formula II may be prepared by reaction of a compound of formula IV with 1,1'-carbonyldiimidazole of formula V according to the equation $$\underset{(IV)}{\underset{R^4}{\underset{R^5}{R^6}}\underset{NH_2}{\overset{R^7}{\overset{OH}{\bigcirc}}}} + \underset{(V)}{\underset{N}{\overset{O}{\underset{\parallel}{C}}}\underset{N}{N}} \longrightarrow$$

$$\underset{(II)}{\underset{R^4}{\underset{R^5}{R^6}}\underset{H}{\overset{R^7}{\overset{O}{\bigcirc}}}\overset{O}{\underset{N}{\bigcirc}}}$$

This reaction may be carried out in an inert solvent at a temperature comprised between 0 and 100° C.

Compounds of formula IV may be prepared by reduction of a compound of formula VI according to procedures known to the person skilled in the art.

$$\underset{(VI)}{\underset{R^4}{\underset{R^5}{R^6}}\underset{NO_2}{\overset{R^7}{\overset{OH}{\bigcirc}}}}$$

Compounds of formula VI are available either commercially or using procedures known to the person skilled in the art.

According to another embodiment, some compounds having the general formula I may be prepared by halogenation of the corresponding compound of formula I wherein $R^6$ is a hydrogen atom with a N-halosuccinimide or any suitable halogenation agent according to the procedure described in: Castanet A.-S., Colobert F., Broutin P.-E., Tetrahedron Lett. (2002), 43, 5047-5048.

According to another embodiment, some compounds having the general formula I may be prepared by halogenation of the corresponding compound of formula I wherein $R^4$ is a hydrogen atom and $R^6$ is different from hydrogen with a N-halosuccinimide or any suitable halogenation agent according to the procedure described in: Castanet A.-S., Colobert F., Broutin P.-E., Tetrahedron Lett. (2002), 43, 5047-5048.

In one embodiment, the present invention concerns also the synthesis intermediates selected from the group consisting of 5,6-difluoro-1,3-benzoxazol-2(3H)-one and 7-bromo-1,3-benzoxazol-2(3H)-one.

It has now been found that compounds of formula Ia, their pharmaceutically acceptable salts, or stereoisomeric forms thereof.

It has now been found that compounds of formula Ia, their pharmaceutically acceptable salts, or stereoisomeric forms thereof (Ia)

wherein
$R^1$ is hydrogen or $C_{1-4}$-alkyl unsubstituted or substituted by hydroxy;
$R^2$ is hydrogen or $C_{1-4}$-alkyl unsubstituted or substituted by hydroxy;
$R^3$ is hydrogen or unsubstituted $C_{1-4}$-alkyl;
$R^{3a}$ is hydrogen or unsubstituted $C_{1-4}$-alkyl;
$R^4$ is hydrogen, halogen, or $C_{1-4}$-alkoxy unsubstituted or substituted by a phenyl group;
$R^5$ is hydrogen, halogen, or $C_{1-4}$-alkoxy unsubstituted or substituted by a phenyl group;
$R^6$ is hydrogen, halogen, or $C_{1-4}$-alkoxy unsubstituted or substituted by a phenyl group;
$R^7$ is hydrogen, halogen, or $C_{1-4}$-alkoxy unsubstituted or substituted by a phenyl group;
are useful in a variety of pharmaceutical indications.

For example, the compounds of formula Ia according to the invention are useful for the symptomatic and/or prophylactic treatment of movement disorders and/or motor fluctuations, in particular in Parkinson's disease.

In another aspect the invention therefore provides the therapeutical use of compounds of formula Ia, or pharmaceutically acceptable salts thereof, (Ia)

wherein
$R^1$ is hydrogen or $C_{1-4}$-alkyl unsubstituted or substituted by hydroxy;
$R^2$ is hydrogen or $C_{1-4}$-alkyl unsubstituted or substituted by hydroxy;
$R^3$ is hydrogen or unsubstituted $C_{1-4}$-alkyl;
$R^{3a}$ is hydrogen or unsubstituted $C_{1-4}$-alkyl;
$R^4$ is hydrogen, halogen, or $C_{1-4}$-alkoxy unsubstituted or substituted by a phenyl group;
$R^5$ is hydrogen, halogen, or $C_{1-4}$-alkoxy unsubstituted or substituted by a phenyl group;

R⁶ is hydrogen, halogen, or $C_{1-4}$-alkoxy unsubstituted or substituted by a phenyl group;

R⁷ is hydrogen, halogen, or $C_{1-4}$-alkoxy unsubstituted or substituted by a phenyl group.

In a particular embodiment, the invention provides the therapeutical use of compounds of formula I, or pharmaceutically acceptable salts thereof,

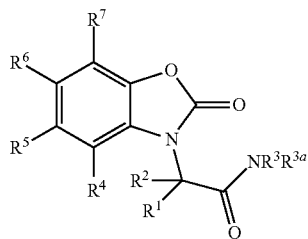

(I)

wherein

R¹ is hydrogen or $C_{1-4}$-alkyl unsubstituted or substituted by hydroxy;

R² is hydrogen or $C_{1-4}$-alkyl unsubstituted or substituted by hydroxy;

R³ is hydrogen or unsubstituted $C_{1-4}$-alkyl;

R³ᵃ is hydrogen or unsubstituted $C_{1-4}$-alkyl;

R⁴ is hydrogen, halogen, or $C_{1-4}$-alkoxy unsubstituted or substituted by a phenyl group;

R⁵ is hydrogen, halogen, or $C_{1-4}$-alkoxy unsubstituted or substituted by a phenyl group;

R⁶ is hydrogen, halogen, or $C_{1-4}$-alkoxy unsubstituted or substituted by a phenyl group;

R⁷ is hydrogen, halogen, or $C_{1-4}$-alkoxy unsubstituted or substituted by a phenyl group;

with the proviso that if R¹, R², R⁴, R⁵ and R⁷ are hydrogen, then R⁶ is not hydrogen, bromo or chloro; and if R¹, R², R⁴, R⁶ and R⁷ are hydrogen, then R⁵ is not bromo or chloro; and if R¹, R², R³, R⁴ and R⁷ are hydrogen, R⁶ is bromo, and R⁵ is chloro, then R³ᵃ is not methyl.

The invention also provides the therapeutical use of the compound 2-(6-bromo-2-oxo-1,3-benzoxazol-3(2H)-yl)-N,N-dimethylacetamide, or of its pharmaceutically acceptable salts.

In a preferred embodiment, the invention provides the therapeutical use of compounds of formula Ia, or pharmaceutically acceptable salts thereof,
wherein
R¹ is hydrogen;
R² is hydrogen;
R³ is selected from hydrogen or unsubstituted $C_{1-4}$-alkyl;
R³ᵃ is selected from hydrogen or unsubstituted $C_{1-4}$-alkyl;
R⁴ is hydrogen;
R⁵ is selected from hydrogen, bromo or chloro;
R⁶ is selected from hydrogen, bromo or chloro and
R⁷ is hydrogen.

In a preferred embodiment, the invention provides the therapeutical use of a compound of formula Ia selected from 2-(6-bromo-2-oxo-1,3-benzoxazol-3(2H)-yl)-N,N-dimethylacetamide; 2-(2-oxo-1,3-benzoxazol-3(2H)-yl)acetamide; 2-(6-bromo-2-oxo-1,3-benzoxazol-3(2H)-yl)acetamide; 2-(6-chloro-2-oxo-1,3-benzoxazol-3(2H)-yl)acetamide; 2-(6-chloro-2-oxo-1,3-benzoxazol-3(2H)-yl)-N,N-dimethylacetamide; and N,N-dimethyl-2-(2-oxo-1,3-benzoxazol-3(2H)-yl)acetamide.

In a more preferred embodiment, the invention provides the therapeutical use of a compound of formula Ia selected from 2-(6-bromo-2-oxo-1,3-benzoxazol-3(2H)-yl)-N,N-dimethylacetamide; 2-(2-oxo-1,3-benzoxazol-3(2H)-yl)acetamide; and 2-(6-chloro-2-oxo-1,3-benzoxazol-3(2H)-yl)acetamide.

In a most preferred embodiment, the invention provides the therapeutical use of a compound of formula Ia selected from 2-(2-oxo-1,3-benzoxazol-3(2H)-yl)acetamide and 2-(6-chloro-2-oxo-1,3-benzoxazol-3(2H)-yl)acetamide.

In another embodiment, the invention provides a pharmaceutical composition comprising a compound of formula Ia, its pharmaceutically acceptable salts, or stereoisomeric form thereof

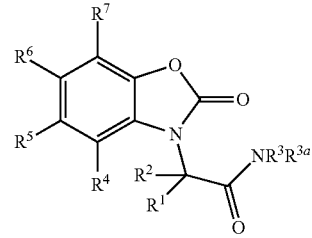

(Ia)

wherein
R¹ is hydrogen or $C_{1-4}$-alkyl unsubstituted or substituted by hydroxy;
R² is hydrogen or $C_{1-4}$-alkyl unsubstituted or substituted by hydroxy;
R³ is hydrogen or unsubstituted $C_{1-4}$-alkyl;
R³ᵃ is hydrogen or unsubstituted $C_{1-4}$-alkyl;
R⁴ is hydrogen, halogen, or $C_{1-4}$-alkoxy unsubstituted or substituted by a phenyl group;
R⁵ is hydrogen, halogen, or $C_{1-4}$-alkoxy unsubstituted or substituted by a phenyl group;
R⁶ is hydrogen, halogen, or $C_{1-4}$-alkoxy unsubstituted or substituted by a phenyl group;
R⁷ is hydrogen, halogen, or $C_{1-4}$-alkoxy unsubstituted or substituted by a phenyl group.

In another aspect the invention provides the use of compounds of formula Ia, or pharmaceutically acceptable salts thereof, for the symptomatic and/or prophylactic treatment of motor fluctuations and/or dyskinesia in Parkinson's patients before or during exposure to dopamine replacement therapy.

The compounds of formula Ia according to the invention may also be used for the treatment and the prevention of idiopathic Parkinson's disease and other Parkinsonian syndromes.

Additionally, the compounds of formula Ia according to the invention may be used for the treatment and the prevention of movement disorders.

The compounds of formula Ia according to the invention may be administered in conjunction with an anti-parkinsonian or any other existing therapy. For example, compounds of formula Ia may be useful as adjunct therapy in Parkinson's disease to reduce the side-effects experienced with those treatments on long term use, including but not limited to L-DOPA (motor fluctuations and dyskinesia). The compounds may also be used where in the anti-parkinsonian therapy is one of cell implantation/transplantation, gene therapy, subthalamic nucleus lesions/deep brain stimulation and GPi lesion/deep brain stimulation.

The compounds of formula Ia may be used to protect against neurodegeneration and may be used in conjunction with neuroprotective agents.

The compounds of formula Ia may be used to treat neuroleptic-induced Parkinsonism and tardive dyskinesia and could be administered in conjunction with antipsychotic agents.

The compounds of formula Ia according to the invention may also be used for the treatment of schizophrenia, or other psychotic disorders.

The compounds of the invention may also be used in the treatment of mood disorders.

The compounds of formula Ia according to the invention may also be used in the treatment of anxiety disorders.

The compounds of formula Ia according to the invention may also be useful in the treatment of substance-related disorders.

The compounds of formula Ia according to the invention may also be used in the treatment of delirium, dementia, amnestic and other cognitive disorders (memory, frontal and attentional problems).

The compounds of formula Ia according to the invention can also be used in the treatment of sexual disorders, sleep disorders, eating disorders (anorexia/bulimia nervosa), personality disorders, factitious disorders, dissociative disorders, emesis, aggression, autism, vertigo, circadian rhythm disorders, convulsion, seizure, epilepsy, gastric motility disorders, attention deficit disorder, reward deficiency syndrome, attention deficit hyperactivity disorder (ADHD), migraine, trigeminal and other neuralgias, chronic pain, neuropathic pain, cerebral ischemia, cardiac arrhythmia, myotonia, stroke, neonatal cerebral haemorrhage, amyotrophic lateral sclerosis, spasticity and degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

Thus, the present invention also concerns a compound having the formula Ia or a pharmaceutically acceptable salt thereof or stereoisomeric forms thereof as defined above for use as a medicament.

In a further aspect, the present invention concerns also the use of a compound of formula Ia or a pharmaceutically acceptable salt thereof for the manufacture of a medicament for the treatment of neurological, psychiatric and other disorders such as mentioned above.

In particular, the present invention concerns the use of a compound of formula Ia or a pharmaceutically acceptable salt thereof for the manufacture of a medicament for the treatment of motor fluctuations and/or dyskinesia in Parkinson's patients before or during exposure to dopamine replacement therapy, idiopathic Parkinson's disease and other Parkinsonian syndromes, movement disorders, psychotic disorders, mood disorders, anxiety disorders, substance-related disorders, delirium and dementia.

The methods of the invention comprise administration to a mammal (preferably human) suffering from above mentioned conditions or disorders, of a compound of formula Ia according to the invention in an amount sufficient to alleviate or prevent the disorder or condition.

The compound is conveniently administered in any suitable unit dosage form, including but not limited to one containing 3 to 5000 mg, preferably 5 to 500 mg of active ingredient per unit dosage form.

The term "treatment" as used herein includes symptomatic treatment, curative treatment and prophylactic treatment.

By "symptomatic" is meant the efficaciousness of the active compound in treating the current episode.

By "curative" is meant efficacy in treating the appearance of symptomatic episodes of a disorder or condition.

By "prophylactic" is meant prevention of the occurrence or recurrence of a disorder or condition. In particular we mean the prevention of any induction of the recurrent episodes and the possibility to depress the manifestation of motor fluctuation and dyskinesia.

By "motor fluctuations" is meant the development in a L-DOPA-treated subject of these four different phenomena: delayed "on" response and dose failures, end of dose wearing off, unpredictable "on-off" response and freezing episodes.

By "end-of-dose wearing off" is meant the loss of response to a dose of medication before taking the next dose.

The term "dyskinesia" is defined as the development in a subject of abnormal involuntary movements. This appears in patients with Huntington's disease, in Parkinson's disease patients exposed to chronic dopamine replacement therapy, and in Schizophrenia patients exposed to chronic treatment with neuroleptics. Dyskinesias, as a whole, are characterised by the development in a subject of abnormal involuntary movements. One way in which dyskinesias may arise is as a side effect of dopamine replacement therapy for parkinsonism or other basal ganglia-related movement disorders.

The terms "idiopathic Parkinson's disease and other Parkinsonian syndromes", include, but are not limited to genetic Parkinsonisms, multiple system atrophy, progressive supranuclear palsy, corticobasal degeneration, Fahr's disease, post-encephalitic parkinsonism, parkinsonism resulting from head injury, drug induced parkinsonisms (e.g. following treatment of schizophrenia and other psychiatric disorders), drug intoxication (e.g. with MPTP-contaminated heroin), toxin-induced Parkinsonism (e.g. following carbon monoxide or manganese poisoning), treatment of Wilson's disease, vascular Parkinsonism, and other Parkinsonian syndromes.

The term "Parkinsonian syndrome" relates to a syndrome characterized by slowness of movement (bradykinesia), rigidity and/or tremor. Parkinsonian syndromes are seen in a variety of conditions, most commonly in idiopathic Parkinsonism (i.e. Parkinson's Disease) but also following treatment of schizophrenia, exposure to toxins/drugs and head injury. It is widely appreciated that the primary pathology underlying Parkinson's disease is degeneration, in the brain, of the dopaminergic projection from the substantia nigra to the striatum. This has led to the widespread use of dopamine-replacing agents (e.g. L-DOPA and dopamine agonists) as symptomatic treatments for Parkinson's disease and such treatments have been successful in increasing the quality of life of patients suffering from Parkinson's disease. However, dopamine-replacement treatments do have limitations, especially following long-term treatment. Problems can include a wearing-off of the anti-parkinsonian efficacy of the treatment and the appearance of a range of side-effects which manifest as abnormal involuntary movements, such as dyskinesias.

By "movement disorder" is meant neurological motor disorders manifested by slowness or poverty of movement (bradykinesia or hypokinesia, such as that seen in parkinsonian disorders) at one end of the spectrum and abnormal involuntary movement (hyperkinesias) such as tremor, dystonia, athetosis, chorea, ballismus, tics, myoclonus, restless legs syndrome, stereotypies, akathisias, and other dyskinesias at the other. Movement disorders include, but are not limited to tremors (e.g. physiological, essential, dystonic, primary writing, orthostatic, neuropathic, cerebellar tremor, etc.), choreas (e.g. in Huntingston's disease, Haw River syndrome, neuroacanthocytosis, McLeod syndrome, benign hereditary chorea, Sydenham's chorea, ballismus, senile chorea, etc.), tardive dyskinesia, the dystonias (e.g. childhood onset generalized primary dystonia, adult-onset primary focal and segmental dystonia, X-linked dystonia-Parkinsonism, dopa-responsive dystonia, rapid-onset dystonia, post-traumatic dystonia, tardive dystonia, paroxysmal kinesigenic dyskinesia, paroxysmal nonkinesigenic dyskinesia, secondary paroxysmal dyskinesia, and other paroxysmal dyskinesias, etc.), tics including Tourette's syndrome and adult-onset tic disorders, post-infectious autoimmune neuropsychiatric disorders associated with streptococcal exposure (PANDAS), myoclonic disorders (e.g. essential, posthypoxic, startle, spinal, propriospinal, toxin- and drug-induced myoclonus etc.), and other movement disorders such as hemifacial spasm, stiff person syndrome, painful legs-moving toes syndrome and restless legs syndrome.

The term "psychotic disorders" includes but is not limited to schizophrenia, schizophreniform disorder, schizoaffective disorder, delusional disorder, brief psychotic disorder, shared psychotic disorder, psychotic disorder due to a general medical condition, substance-induced psychotic disorder, postpartum psychiatric syndromes, and psychotic disorder not otherwise specified.

The term "mood disorders" includes but is not limited to depression, major depressive disorder, dysthimic disorder, depression disorder not otherwise specified, mania, bipolar I disorder, bipolar II disorder, cyclothymic disorder, bipolar disorder not otherwise specified, mood disorder due to a general medical condition, substance-induced mood disorder, mood disorder not otherwise specified, The term "anxiety disorders" includes but is not limited to panic attack, agoraphobia, panic disorder with/without agoraphobia, agoraphobia without history of panic disorder, specific phobia, social phobia, obsessive-compulsive disorder, posttraumatic stress disorder, acute stress disorder, generalized anxiety disorder, anxiety disorder due to a general medical condition, substance-induced anxiety disorder, anxiety disorder not otherwise specified.

The term "substance-related disorders" includes more specifically substance use disorders (substance dependence, substance abuse), substance-induced disorders (substance intoxication, substance withdrawal, substance-induced mental disorders), alcohol-related disorders, amphetamine-related disorders, caffeine-related disorders, cannabis-related disorders, cocaine-related disorders, hallucinogen-related disorders, inhalant-related disorders, nicotine-related disorders, opioid related disorders, phencyclidine-related disorders, sedative-hypnotic or anxiolytic-related disorders, other (unknown) substance-related disorders.

The term "delirium" refers to a disturbance of consciousness and a change in cognition that develop over a short period of time (delirium due to a general medical condition, substance-induced delirium, delirium due to multiple etiologies, delirium not otherwise specified).

The term "dementia" refers to multiple cognitive deficits that include impairment in memory. It includes but is not limited to Alzheimer's type dementia, vascular dementia, dementia due to HIV disease, head trauma, Parkinson's disease (including dementia with Lewy bodies), Huntington's disease, Pick's disease, Creutzfedlt-Jacob disease or other medical conditions, substance-induced persisting dementia, dementia due to multiple etiologies or not otherwise specified.

The term "amnestic disorders" as used herein refers to a disturbance in memory that is either due to the direct physiological effects of a general medical condition or due to the persisting effects of a substance.

The term "epilepsy" as used herein refers to a chronic neurologic condition characterised by unprovoked, recurrent epileptic seizures. An epileptic seizure is the manifestation of an abnormal and excessive synchronised discharge of a set of cerebral neurons; its clinical manifestations are sudden and transient. The term "epilepsy" as used herein can also refer to a disorder of brain function characterised by the periodic occurrence of seizures. Seizures can be "nonepileptic" when evoked in a normal brain by conditions such as high fever or exposure to toxins or "epileptic" when evoked without evident provocation.

The term "seizure" as used herein refers to a transient alteration of behaviour due to the disordered, synchronous, and rhythmic firing of populations of brain neurones.

The term "migraine" as used herein means a disorder characterised by recurrent attacks of headache that vary widely in intensity, frequency, and duration. The attacks are commonly unilateral and are usually associated with anorexia, nausea, vomiting, phonophobia, and/or photophobia. In some cases they are preceded by, or associated with, neurological and mood disturbances. Migraine headache may last from 4 hours to about 72 hours. The International Headache Society (IHS, 1988) classifies migraine with aura (classical migraine) and migraine without aura (common migraine) as the major types of migraine. Migraine with aura consists of a headache phase preceded by characteristic visual, sensory, speech, or motor symptoms. In the absence of such symptoms, the headache is called migraine without aura.

The term "bipolar disorders" as used herein refers to those disorders classified as Mood Disorders according to the Diagnostic and Statistical Manual of Mental Disorders, 4th edition (Diagnostic and Statistical Manual of Mental Disorders (DSM-IV TM), American Psychiatry Association, Washington, D.C., 1994). Bipolar disorders are generally characterised by spontaneously triggered repeated (i.e. at least two) episodes in which the patient's hyperexcitability, activity and mood are significantly disturbed, this disturbance consisting on some occasions of an elevation of mood and increased energy and activity (mania or hypomania), and in other occasions a lowering of mood and decreased energy and activity (depression). Bipolar disorders are separated into four main categories in the DSM-IV (bipolar I disorder, bipolar II disorder, cyclothymia, and bipolar disorders not otherwise specified).

The term "manic episode", as used herein refers to a distinct period during which there is an abnormally and persistently elevated, expansive, or irritable mood with signs of pressured speech and psychomotor agitation.

The term "hypomania", as used herein refers to a less extreme manic episode, with lower grade of severity.

The term "major depressive episode", as used herein refers to a period of at least 2 weeks during which there is either depressed mood or the loss of interest or pleasure in nearly all activities with signs of impaired concentration and psychomotor retardation.

The term "mixed episode", as used herein refers to a period of time (lasting at least 1 week) in which the criteria are met both for a manic episode and for a major depressive episode nearly every day.

The term "chronic pain" as used herein refers to the condition gradually being recognised as a disease process distinct from acute pain. Conventionally defined as pain that persists beyond the normal time of healing, pain can also be considered chronic at the point when the individual realizes that the pain is going to be a persistent part of their lives for the foreseeable future. It is likely that a majority of chronic pain syndromes involves a neuropathic component, which is usually harder to treat than acute somatic pain.

The term "neuropathic pain" as used herein refers to pain due to a dysfunctional nervous system, sometimes occurring following injury to the central nervous system (central pain), but more often caused by damage to peripheral nerves (painful peripheral neuropathy). Neuropathic pain is most likely caused by neural hyperexcitation in partially damaged nerves. Several types of painful peripheral neuropathy, which may share some underlying pathogenic mechanisms, have been distinguished, such as: (1) posttraumatic painful peripheral neuropathy; (2) phantom limb pain; (3) facial (trigeminal) pains; (4) postherpetic neuralgia; (5) painful diabetic neuropathy; (6) neuropathies due to cancer tumors; (7) neuropathies induced by treatment with anti-neoplastic agents; and (8) nerve damage associated with demyelinating disease, such as multiple sclerosis. In neuropathic pain, painful reactions appear in response to normally neutral stimuli (allodynia) or as exaggerated reactions to painful stimuli (hyperalgesia). Spontaneous pain, not provoked by external stimuli, also occurs in neuropathic pain, and is the most difficult form of pain to measure and treat.

The term "tics" refers to common and often disabling neurological disorders. They are frequently associated with behaviour difficulties, including obsessive-compulsive disorder, attention deficit hyperactivity disorder and impulse control. Tics are involuntary, sudden, rapid, repetitive, nonrhythmic stereotypic movements or vocalizations. Tics are manifested in a variety of forms, with different durations and degrees of complexity. Simple motor tics are brief rapid movements that often involve only one muscle group. Complex motor tics are abrupt movements that involve either a cluster of simple movements or a more coordinated sequence of movements. Simple vocal tics include sounds such as grunting, barking, yelping, and throat clearing. Complex vocal tics include syllables, phrases, repeating other people's words and repeating one's own words.

The term "tremor" refers to an involuntary, rhythmical, oscillatory movement of a body part. Tremor can be phenomenologically defined as tremor at rest or associated with an action. Such an action can be postural (maintenance of a limb position), kinetic (movement-related), or intentional (at the end of a purposeful movement). Etiologically, tremor most often occurs in Parkinson's disease (Parkinsonian rest tremor) and in essential tremor (postural and kinetic tremor), which consists of hereditary and age-related forms. Tremor may also occur in dystonia and in multiple sclerosis. Other tremors, which can arise from various etiologies, are cerebellar (intentional tremor) and Holmes' midbrain tremor (postural tremor). Tremor can also be an exaggerated form of normal physiological tremor. Apart from the behavioural context in which tremor occurs, tremor frequency is an important criterion to distinguish between various forms of tremor. Essential tremor has the highest incidence of all tremors. As it is age-related, it can be expected to increase in aging populations. Animal models and clinical data indicate that essential tremor may be primarily based on a brainstem (inferior olivary nucleus)—cerebellar dysfunction, whereas Parkinsonian tremor probably originates from abnormal activity within the basal ganglia. Excessive synchronization and/or hyperexcitation in neuronal circuits may underlie tremor activity.

The compounds of formula Ia according to the invention may advantageously be used in conjunction with one or more other therapeutic agents. In particular the compounds according to the invention may be used in conjunction with one or more other therapeutic agents linked to the cholinergic transmission: e.g. agonists/antagonists to M1, M2, M3, M4, M5 receptors and to nicotinic receptors, and acetylcholinesterase modulators.

The compounds of formula Ia according to the invention may be used in conjunction with one or more other therapeutic agents linked to the adrenergic/noradrenergic transmission: e.g. agonists/antagonists to $\alpha1$, $\alpha2$, $\alpha1$, $\alpha2$, $\alpha3$ receptors, MAO (type A and B) and COMT modulators.

The compounds of formula Ia according to the invention may be used in conjunction with one or more other therapeutic agents linked to dopaminergic transmission: e.g. agonists/antagonists to dopamine D1, D2, D3, D4, and D5 receptors, tyrosine-hydroxylase and DOPA-decarboxylase modulators, and vesicle monoamines transporters modulators.

The compounds of formula Ia according to the invention may be used in conjunction with one or more other therapeutic agents linked to serotoninergic transmission: e.g. agonists/antagonists to $5\text{-HT}_1$, $5\text{-HT}_2$, $5\text{-HT}_3$, $5\text{-HT}_4$, $5\text{-HT}_5$, $5\text{-HT}_6$ and $5\text{-HT}_7$ receptors.

The compounds of formula Ia according to the invention may be used in conjunction with one or more other therapeutic agents linked to histaminergic transmission: e.g. agonists/antagonists to $H_1$, $H_2$, $H_3$ and $H_4$ receptors.

The compounds of formula Ia according to the invention may be used in conjunction with one or more other therapeutic agents linked to glutamatergic transmission: e.g. agonists/antagonists to AMPA receptors (GluR1, GluR2, GluR3, GluR4); kainate receptors (GluR5, GluR6, GluR7 and KA1, KA2); NMDA receptors (subunits NR1, NR2A, NR2B, NR2C, NR2D and NR3A).

The compounds of formula Ia according to the invention may be used in oconjunction with one or more other therapeutic agents linked to gabaergic transmission: e.g. agonists/antagonists to $GABA_{A1}$ to $GABA_{A6}$, $GABA_{AO}$, $GABA_C$ and $GABA_B$, or agents enhancing the production or reducing the degradation or the re-uptake of GABA such as vaproate, vigabatrin or tiagabine.

The compounds of formula Ia according to the invention may be used in conjunction with one or more other therapeutic agents such as $CB_1$ agonists, VR1 agonists, SV2 ligands such as levetiracetam, brivaracetam or seletracetam, amantadine, or NMDA/AMPA antagonists.

Activity in any of the above-mentioned indications can of course be determined by carrying out suitable clinical trials in a manner known to a person skilled in the relevant art for the particular indication and/or in the design of clinical trials in general.

For treating diseases, compounds of formula Ia or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula Ia or pharmaceutically acceptable salts thereof in combination with a pharmaceutically acceptable diluent or carrier.

To prepare a pharmaceutical composition according to the invention, one or more of the compounds of formula Ia or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally or parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula Ia in compositions for oral administration is at least 0.5% by weight and can be up to 80% by weight with respect to the total weight of the composition.

For the preferred oral compositions, the daily dosage is in the range 5 to 5000 milligrams (mg) of compounds of formula Ia.

In compositions for parenteral administration, the quantity of compound of formula I' present is at least 0.5% by weight and can be up to 33% by weight with respect to the total weight of the composition. For the preferred parenteral compositions, the dosage unit is in the range 5 mg to 5000 mg of compounds of formula Ia.

The daily dose can fall within a wide range of dosage units of compound of formula Ia and is generally in the range 3 to 7000 mg, and preferably 5 to 5000 mg. However, it should be understood that the specific doses can be adapted to particular cases depending on the individual requirements, at the physician's discretion.

The following examples are provided for illustrative purposes.

Unless specified otherwise in the examples, characterization of the compounds is performed according to the following methods:

NMR spectra are recorded on a BRUKER AC 250 Fourier Transform NMR Spectrometer fitted with an Aspect 3000 computer and a 5 mm $^1H/^{13}C$ dual probehead or BRUKER DRX 400 FT NMR fitted with a SG Indigo$^2$ computer and a 5 mm inverse geometry $^1H/^{13}C/^{15}N$ triple probehead. The compound is studied in DMSO-$d_6$ (or CDCl$_3$) solution at a probe temperature of 313 K or 300 K and at a concentration of 20 mg/ml. The instrument is locked on the deuterium signal of DMSO-$d_6$ (or CDCl$_3$). Chemical shifts are given in ppm downfield from TMS taken as internal standard.

HPLC analyses are performed using one of the following systems:
- an Agilent 1100 series HPLC system mounted with an INERTSIL ODS 3 C18, DP 5 µm, 250×4.6 mm column. The gradient runs from 100% solvent A (acetonitrile, water, H$_3$PO$_4$ (5/95/0.001, v/v/v)) to 100% solvent B (acetonitrile, water, H$_3$PO$_4$ (95/5/0.001, v/v/v)) in 6 min with a hold at 100% B of 4 min. The flow rate is set at 2.5 ml/min. The chromatography is carried out at 35° C.
- a HP 1090 series HPLC system mounted with a HPLC Waters Symetry C18, 250×4.6 mm column. The gradient runs from 100% solvent A (MeOH, water, H$_3$PO$_4$ (15/85/0.001 M, v/v/M)) to 100% solvent B (MeOH, water, H$_3$PO$_4$ (85/15/0.001 M, v/v/M)) in 10 min with a hold at 100% B of 10 min. The flow rate is set at 1 ml/min. The chromatography is carried out at 40° C.

Mass spectrometric measurements in LC/MS mode are performed as follows:

HPLC conditions

Analyses are performed using a WATERS Alliance HPLC system mounted with an INERTSIL ODS 3, DP 5 µm, 250×4.6 mm column.

The gradient runs from 100% solvent A (acetonitrile, water, TFA (10/90/0.1, v/v/v)) to 100% solvent B (acetonitrile, water, TFA (90/10/0.1, v/v/v)) in 7 min with a hold at 100% B of 4 min. The flow rate is set at 2.5 ml/min and a split of ⅕ is used just before API source.

MS Conditions

Samples are dissolved in acetonitrile/water, 70/30, v/v at the concentration of about 250 µgr/ml. API spectra (+ or −) are performed using a FINNIGAN (San Jose, Calif., USA) LCQ ion trap mass spectrometer. APCI source operates at 450° C. and the capillary heater at 160° C. ESI source operates at 3.5 kV and the capillary heater at 210° C.

Mass spectrometric measurements in DIP/EI mode are performed as follows: samples are vaporized by heating the probe from 50° C. to 250° C. in 5 min. EI (Electron Impact) spectra are recorded using a FINNIGAN (San Jose, Calif., USA) TSQ 700 tandem quadrupole mass spectrometer. The source temperature is set at 150° C.

Mass spectrometric measurements on a TSQ 700 tandem quadrupole mass spectrometer (Finnigan MAT, San Jose, Calif., USA) in GC/MS mode are performed with a gas chromatograph model 3400 (Varian, Walnut Creek, Calif., USA) fitted with a split/splitless injector and a DB-5MS fused-silica column (15 m×0.25 mm I.D., 1 µm) from J&W Scientific (Folsom, Calif., USA). Helium (purity 99.999%) is used as carrier gas. The injector (CTC A200S autosampler) and the transfer line operate at 290 and 250° C., respectively. Sample (1 µl) is injected in splitless mode and the oven temperature is programmed as follows: 50° C. for 5 min., increasing to 280° C. (23° C./min) and holding for 10 ml. The TSQ 700 spectrometer operates in electron impact (EI) or chemical ionization (CI/CH$_4$) mode (mass range 33-800, scan time 1.00 sec). The source temperature is set at 150° C.

Preparative chromatographic separations are performed on silicagel 60 Merck, particle size 15-40 µm, reference 1.15111.9025, using Novasep axial compression columns (80 mm i.d.), flow rates between 70 and 150 ml/min. Amount of silicagel and solvent mixtures as described in individual procedures.

The following abbreviations are used in the examples:

| | |
|---|---|
| AcOEt | Ethyl acetate |
| CH$_3$CN | Acetonitrile |
| DMF | N,N-Dimethylformamide |
| NBS | N-bromosuccinimide |
| NCS | N-chlorosuccinimide |
| TFA | Trifluoroacetic acid |
| THF | Tetrahydrofuran |

EXAMPLE 1

Synthesis of 2-(7-fluoro-2-oxo-1,3-benzoxazol-3 (2H)-yl)acetamide 12

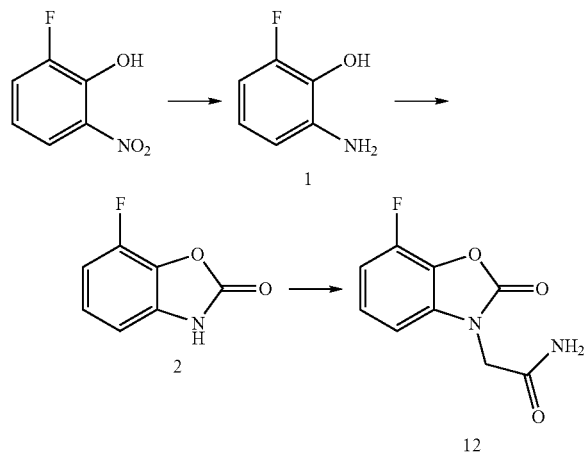

1.1 Synthesis of 2-amino-6-fluorophenol 1

In a three neck flask, fitted with a magnetic stirrer, under inert atmosphere, a suspension of 2-fluoro-6-nitrophenol (5 g, 31.83 mmol), ammonium formate (6 g, 95.50 mmol) and Pd—C (10% w/w, 0.34 g, 3.2 mmol) in MeOH (100 ml) is stirred 0.5 h at room temperature. The reaction mixture is filtered through celite and concentrated in vacuo to give 2-amino-6-fluorophenol 1 (4 g) which is used in the next step without any further purification.

$^1$H NMR ((CD$_3$)$_2$SO, 250 MHz): 4.66-4.98 (s (broad), 2H); 6.315 (ddd, J: 1.51; 8.10 and 10.57 Hz, 1H); 6.41 (ddd, J: 1.30, 1.30 and 8.10 Hz, 1H); 6.52 (ddd, J: 5.80, 8.10 and 8.10 Hz, 1H); 8.60-9.40 (s(broad), 1H).

1.2 Synthesis of 7-fluoro-1,3-benzoxazol-2(3H)-one 2

In a three neck flask, fitted with a magnetic stirrer, under inert atmosphere, 1,1-carbonyldiimidazole (15.6 g, 96 mmol) is added to a solution of 2-amino-6-fluorophenol 1 (4 g, 32 mmol) in 100 ml of anhydrous tetrahydrofuran at room temperature. The solution is refluxed for 1 h, cooled down to room temperature and concentrated in vacuo. The crude reaction mixture is purified by chromatography on silicagel (n-hexane/AcOEt:1/1 (v/v)) to afford 7-fluoro-1,3-benzoxazol-2(3H)-one 2.

Yield: 5.76 g (86%).

$^1$H NMR ((CD$_3$)$_2$SO, 250 MHz): 6.95 (d(broad), J: 7.80 Hz, 1H); 7.03 (dd, J 5.00 and 7.80 Hz, 1H); 7.15 (ddd, J: 5.03, 8.56 and 13.60 Hz, 1H).

Compounds listed in table 1 can be synthesized according to the same method. Table 1:

| No | IUPAC Name |
|---|---|
| 3 | 6-methoxy-1,3-benzoxazol-2(3H)-one |
| 4 | 6-fluoro-1,3-benzoxazol-2(3H)-one |
| 5 | 5,6-difluoro-1,3-benzoxazol-2(3H)-one |
| 6 | 7-chloro-1,3-benzoxazol-2(3H)-one |
| 7 | 6,7-difluoro-1,3-benzoxazol-2(3H)-one |
| 8 | 7-bromo-1,3-benzoxazol-2(3H)-one |
| 9 | 7-methoxy-1,3-benzoxazol-2(3H)-one |

1.3 Synthesis of 2-(7-fluoro-2-oxo-1,3-benzoxazol-3 (2H)-yl)acetamide 12

In a three neck flask, fitted with a magnetic stirrer, under inert atmosphere, NaH (in oil, 60 w/w, 1.8 g, 45.15 mmol) is carefully added by portion into a solution of 7-fluoro-1,3-benzoxazol-2(3H)-one 2 (5.76 g, 37.62 mmol) in dried DMF (80 ml) at 0° C. After 0.25 h, 2-bromo-acetamide (6.22 g, 45.15 mmol) is added. The reaction mixture is stirred for 1 h at room temperature, quenched with water, concentrated in vacuo and the residue is recrystallized in EtOH/H$_2$O (80/20 (v/v)) to afford 2-(7-fluoro-2-oxo-1,3-benzoxazol-3(2H)-yl) acetamide.

Yield: 3.12 g (40%).

MS (LC-MS, MH$^+$): 211.

EXAMPLE 2

Synthesis of 2-(6-chloro-7-fluoro-2-oxo-1,3-benzoxazol-3(2H)-yl)acetamide 19

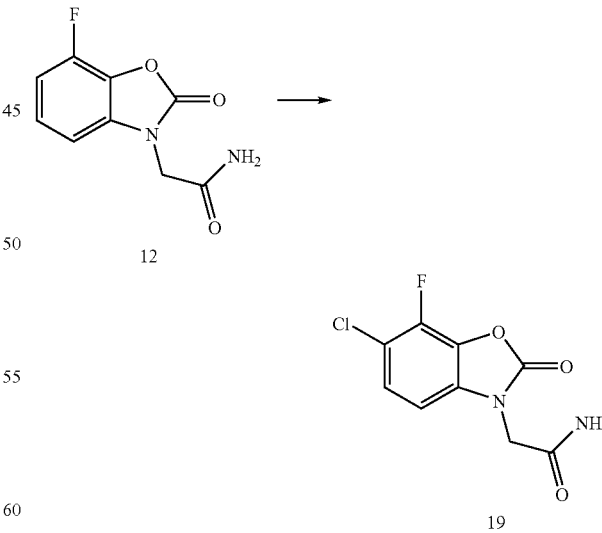

In a three neck flask, fitted with a magnetic stirrer, under inert atmosphere, N-chlorosuccinimide (0.635 g, 4.75 mmol) is added to a suspension of 2-(7-fluoro-2-oxo-1,3-benzoxazol-3(2H)-yl)acetamide 12 (1 g, 4.75 mmol) and sulfuric acid (90% w/w; 20 ml) at 0° C. The reaction is stirred 5 days then poured carefully into ice. The precipitate is collected by filtration and washed with water. The residue is recrystallized in EtOH/water (20/80 (v/v)) to afford 0.54 g of 2-(6-chloro-7-fluoro-2-oxo-1,3-benzoxazol-3(2H)-yl)acetamide 19.

Yield: 0.54 g (47%).

MS (LC-MS, MH$^+$): 245/247.

EXAMPLE 3

Synthesis of 2-(4-chloro-6,7-difluoro-2-oxo-1,3-benzoxazol-3(2H)-yl)acetamide 24

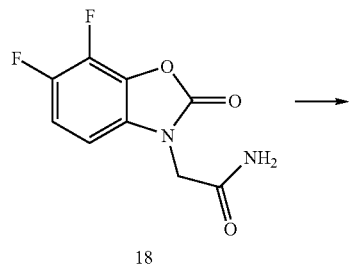

In a three neck flask, fitted with a magnetic stirrer, under inert atmosphere, N-chlorosuccinimide (0.29 g; 2.19 mmol) is added to a suspension of 2-(6,7-difluoro-2-oxo-1,3-benzoxazol-3(2H)-yl)acetamide 18 (0.5 g, 2.19 mmol) and sulfuric acid (90% w/w, 20 ml) at 0° C. The reaction mixture is stirred at room temperature for two days and another portion of N-chlorosuccinimide (0.29 g, 2.19 mmol) is added. After 14 days at room temperature, the reaction mixture is poured carefully into ice. The precipitate is collected by filtration, washed with water and recrystallized EtOH/water (20/80 (v/v)) to afford 0.42 g of a powder which is further purified by column chromatography on reverse phase to give 2-(4-chloro-6,7-difluoro-2-oxo-benzooxazol-3-yl)-acetamide 24 after recrystallization in ethanol.

Yield: 0.163 g (30%).

MS (LC-MS, MH$^+$): 261-263.

Compounds described in table 2 may be prepared according to one of the previous methods.

TABLE 2

Compounds of formula I.

| n° | Configuration | IUPAC Name | MS(LC-MS, MH$^+$) |
|---|---|---|---|
| 10 | achiral | 2-(6-methoxy-2-oxo-1,3-benzoxazol-3(2H)-yl)acetamide | 223 |
| 11 | achiral | 2-(6-fluoro-2-oxo-1,3-benzoxazol-3(2H)-yl)acetamide | 210 (GC-MS, M$^{+\cdot}$) |
| 12 | achiral | 2-(7-fluoro-2-oxo-1,3-benzoxazol-3(2H)-yl)acetamide | 211 |
| 13 | achiral | 2-(5,6-difluoro-2-oxo-1,3-benzoxazol-3(2H)-yl)acetamide | 229 |
| 14 | achiral | 2-(6-bromo-7-fluoro-2-oxo-1,3-benzoxazol-3(2H)-yl)acetamide | 289/291 |
| 15 | achiral | 2-(7-chloro-2-oxo-1,3-benzoxazol-3(2H)-yl)acetamide | 227/229 |
| 16 | achiral | 2-(6-bromo-7-chloro-2-oxo-1,3-benzoxazol-3(2H)-y)acetamide | 305/307/309 |
| 17 | achiral | 2-(6,7-dichloro-2-oxo-1,3-benzoxazol-3(2H)-yl)acetamide | 261/263/265 |
| 18 | achiral | 2-(6,7-difluoro-2-oxo-1,3-benzoxazol-3(2H)-yl)acetamide | 229 |
| 19 | achiral | 2-(6-chloro-7-fluoro-2-oxo-1,3-benzoxazol-3(2H)-yl)acetamide | 289/291 |
| 20 | achiral | 2-(7-bromo-2-oxo-1,3-benzoxazol-3(2H)-yl)acetamide | 271/273 |
| 21 | achiral | 2-(6,7-dibromo-2-oxo-1,3-benzoxazol-3(2H)-yl)acetamide | 349 |
| 22 | achiral | 2-(7-bromo-6-chloro-2-oxo-1,3-benzoxazol-3(2H)-yl)acetamide | 305/307 |
| 23 | achiral | 2-(7-methoxy-2-oxo-1,3-benzoxazol-3(2H)-yl)acetamide | 223 |
| 24 | achiral | 2-(4-chloro-6,7-difluoro-2-oxo-1,3-benzoxazol-3(2H)-yl)acetamide | 263/265 |
| 25 | achiral | 2-(6-bromo-2-oxo-1,3-benzoxazol-3(2H)-yl)-N,N-dimethylacetamide | 299/301 |

EXAMPLE 4

Pharmacological Testing—Hemi-Parktinsonian Rat Model

The invention is based upon our studies relating the use of active compounds long L-DOPA activity when its action is diminishing in a rat model of Parkinson's e.

This study was designed to investigate whether the compounds of the invention prolong L-DOPA activity using the hemi-parkinsonian rat model.

Using stereotaxic surgery in the rats, 6-hydroxydopamine (6-OHDA), a specific to dopamine nerve cells, is delivered directly along the nigrostriatal pathway al forebrain bundle). Uptake of 6-OHDA leads to the death of dopamine nerve resulting in damage similar to that in PD (the abbreviation "PD" means Parkinson's disease). In the rat, destruction of the nerve cells on one side of the brain creates an imbalance in the basal ganglia that causes the rat to spontaneously turn in a circular fashion towards the destroyed side (ipsilateral rotations). Drugs that stimulate receptor sites normally targeted by dopamine (e.g. dopamine agonist or L-DOPA) cause the rat to turn in a direction opposite to the destroyed side (contralateral rotations). The contralateral rotation response provides a behavioral index of dopamine denervation receptor supersensitivity.

The study was performed on 16 male Sprague-Dawley rats. The animals had an average weight of 270 g at surgery and 350 g during the behavioral experiments. To lesion the ascending dopaminergic nigro-stiratal pathway, rats were anaesthetized with ketamine (75 mg/kg, ip) and xylazine (10 mg/kg, ip) and placed in a stereotaxic frame. 6-OHDA (10 µg/rat) was injected unilaterally into the right medial forebrain bundle.

To protect noradrenergic neurons, rats were pre-treated with imipramine (15 mg/kg, ip). Two weeks after surgery, rats were challenged with 100 mg/kg i.p. L-DOPA using eight identical automated rotometers in order to select them for the test. Only rats showing at least 150 contralateral rotations within 60 min were accepted for the test. The test started one week after the selection.

The testing day, all lesioned animals were put in the testing room 15 minutes for acclimation. Eight rats were injected either with vehicle (DMSO, i.p.) or with test compound (100 µmol/kg, i.p.) 15 minutes before the L-DOPA injection and were replaced in their home cage. After the L-DOPA injection (50 mg/kg, i.p.) they were put directly into the rotometers. Contralateral rotations started to be recorded after a 10-min acclimation period in the arenas.

Analyses were conducted on the data recorded for 120 min. Data were analysed with a mixed-model analysis of variance (ANOVA) incorporating the treatment as between-group factor (treatment: 2 levels: vehicle and test compound) and the successive twelve measurements of contralateral rotations as within-subjects factor (time, 12 levels). The reliabilities of the between-mean differences within a time-sample were assessed with planned contrasts using a F statistic.

The major benefit of test compounds was a prolongation of L-DOPA-induced contralateral rotation during the second hour post-drug administration without rise of the side-effect (abnormal involuntary movements were not increased).

Thus the clinical benefit for test compounds may be as an adjunctive therapy to reduce motor fluctuation (i.e. "end-of-dose wearing off") and thus to increase "on-time" in parkinsonian patients exposed to dopamine-replacement therapy. Additionally, the extension of 'on-time' and the potential for L-DOPA sparing represents a useful de novo therapy to delay the onset of dyskinesia.

The tested compounds were injected i.p. at 100 mmol/kg. They demonstrated a significant ability to prolong L-Dopa-induced rotations in the 6-OHDA rat model during the second hour post administration (61-120 min). During this second one-hour period of the test, the following compounds induced a total number of contralateral rotations comprised between 200 and 500 turns whereas the total number of rotations observed with L-Dopa alone fell dramatically (less than 50 turns).

The invention claimed is:

1. A method for the symptomatic treatment of Parkinson's disease or dopa-responsive dystonia in a patient, the method comprising administering to the patient an effective amount of a compound according to formula Ia:

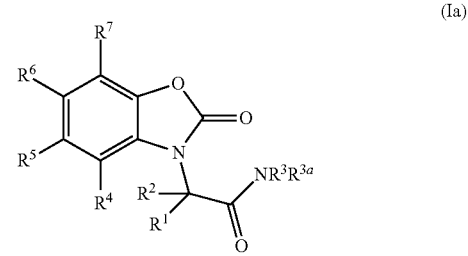

(Ia)

or a pharmaceutically acceptable salt thereof, wherein
$R^1$ is selected from hydrogen or $C_{1-4}$-alkyl unsubstituted or substituted by hydroxy;
$R^2$ is selected from hydrogen or $C_{1-4}$-alkyl unsubstituted or substituted by hydroxy;
$R^3$ is selected from hydrogen or unsubstituted $C_{1-4}$-alkyl;
$R^{3a}$ is selected from hydrogen or unsubstituted $C_{1-4}$-alkyl;
$R^4$ is selected from hydrogen, halogen, or $C_{1-4}$-alkoxy unsubstituted or substituted by a phenyl group;
$R^5$ is selected from hydrogen, halogen, or $C_{1-4}$-alkoxy unsubstituted or substituted by a phenyl group;
$R^6$ is selected from hydrogen, halogen, or $C_{1-4}$-alkoxy unsubstituted or substituted by a phenyl group; and
$R^7$ is selected from hydrogen, halogen, or $C_{1-4}$-alkoxy unsubstituted or substituted by a phenyl group;
with the proviso that the compound is not 2-(6-bromo-2-oxo-1,3-benzoxazol-3(2H)-yl)acetamide.

2. The method according to claim 1 wherein
$R^1$ is hydrogen;
$R^2$ is hydrogen;
$R^3$ is selected from hydrogen or unsubstituted $C_{1-4}$-alkyl;
$R^{3a}$ is selected from hydrogen or unsubstituted $C_{1-4}$-alkyl;
$R^4$ is hydrogen;
$R^5$ is selected from hydrogen, bromo or chloro;
$R^6$ is selected from hydrogen, bromo or chloro; and
$R^7$ is hydrogen;
with the proviso that the compound is not 2-(6-bromo-2-oxo-1,3-benzoxazol-3(2H)-yl)acetamide.

3. The method according to claim 1 wherein the compound is selected from
2-(6-bromo-2-oxo-1,3-benzoxazol-3(2H)-yl)-N,N-dimethylacetamide;
2-(2-oxo-1,3-benzoxazol-3(2H)-yl)acetamide;
2-(6-chloro-2-oxo-1,3-benzoxazol-3(2H)-yl)acetamide;
2-(6-chloro-2-oxo-1,3-benzoxazol-3(2H)-yl)-N,N-dimethylacetamide; and N,N-dimethyl-2-(2-oxo-1,3-benzoxazol-3(2H)-yl)acetamide.

4. The method according to claim 1 wherein
$R^1$ is hydrogen;
$R^2$ is hydrogen;
$R^3$ is selected from hydrogen or methyl;
$R^{3a}$ is selected from hydrogen or methyl;
$R^4$ is hydrogen;
$R^5$ is hydrogen;
$R^6$ is selected from hydrogen, fluoro, chloro, or methoxy; and
$R^7$ is selected from hydrogen, fluoro, chloro, or bromo;
with the proviso that if $R^7$ is hydrogen, then $R^6$ is not hydrogen or chloro.

5. The method according to any one of claim 1-3 or 4 wherein the method is for the symptomatic treatment of Parkinson's disease.

* * * * *